United States Patent
Lee et al.

(10) Patent No.: US 10,137,126 B2
(45) Date of Patent: Nov. 27, 2018

(54) METHOD OF PREPARING VERY SLIGHTLY SOLUBLE DRUG WITH SOLID DOSAGE FORM

(71) Applicant: YUNG SHIN PHARM. IND. CO., LTD., Taichung (TW)

(72) Inventors: Fang-Yu Lee, Taichung (TW); Fu-Yung Lin, Taichung (TW)

(73) Assignee: YUNG SHIN PHARM. IND. CO., LTD., Taichung (TW)

( * ) Notice: Subject to any disclaimer, the term of this patent is extended or adjusted under 35 U.S.C. 154(b) by 15 days.

(21) Appl. No.: 15/081,967

(22) Filed: Mar. 28, 2016

(65) Prior Publication Data

US 2016/0375018 A1 Dec. 29, 2016

(30) Foreign Application Priority Data

Jun. 29, 2015 (TW) .............................. 104120868 A (51) Int. Cl.
*A61K 9/20* (2006.01)
*A61K 31/4985* (2006.01)
*A61K 31/506* (2006.01)
*A61K 31/496* (2006.01)

(52) U.S. Cl.
CPC ........ *A61K 31/4985* (2013.01); *A61K 9/2013* (2013.01); *A61K 9/2018* (2013.01); *A61K 9/2054* (2013.01); *A61K 31/496* (2013.01); *A61K 31/506* (2013.01)

(58) Field of Classification Search
CPC .............. A61K 31/4985; A61K 9/2018; A61K 31/496; A61K 31/506; A61K 9/2013
USPC ...................................................... 424/400
See application file for complete search history.

(56) References Cited

U.S. PATENT DOCUMENTS

| 5,985,326 | A | 11/1999 | Butler |
| 2004/0248901 | A1 | 12/2004 | Lee |
| 2007/0104792 | A1* | 5/2007 | Jenkins ................. A61K 9/14 424/489 |

FOREIGN PATENT DOCUMENTS

| CN | 1138827 A | 12/1996 |
| CN | 1547467 A | 11/2004 |
| CN | 101669942 A | 3/2010 |
| CN | 102309488 A | 1/2012 |
| CN | 103271885 A | 9/2013 |
| CN | 103285401 A | 9/2013 |
| JP | 200148777 A | 2/2001 |
| JP | 2004536108 A | 12/2004 |
| JP | 2006143683 A | 6/2006 |
| WO | 9638131 | 12/1996 |
| WO | 03004060 | 1/2003 |
| WO | 2012039768 A2 | 3/2012 |
| WO | 2012039768 A3 | 3/2012 |
| WO | 2012085927 A2 | 6/2012 |
| WO | 2013177501 A2 | 11/2013 |
| WO | 2013177501 A3 | 11/2013 |
| WO | 2014082651 A1 | 6/2014 |

OTHER PUBLICATIONS

Unknown author, title:Hydroxypropyl methylcellulose phthalate, Chemicla Book; downloaded from http://www.chemicalbook.com/ChemicalProductProperty_EN_CB9257146.htm on May 1, 2018.*
UNknown author; tile: Klucel hydroxypropylcellulose; Ashland: product data; down loaded from https://www.brenntag.com/media/documents/bsi/product_data_sheets/material_science/ashland_cellulose_rheology_modifiers/klucel_hpc_pds.pdf on May 1, 2018.*
Antje S. Uch et al., Use of 1-Methyl-Pyrrolidone as a Solubilizing Agent for Determining the Uptake of Poorly Soluble Drugs, Plenum Publishing Corporation, Pharmaceutical Research, 1999, p. 968-971, vol. 16, No. 6.

* cited by examiner

*Primary Examiner* — Yanzhi Zhang
(74) *Attorney, Agent, or Firm* — Winston Hsu (57) ABSTRACT

A method of preparing a very slightly soluble drug with solid composition includes the following steps: (a) adding a very slightly soluble drug into an organic solvent and polysorbate to form a first solution; (b) adding the first solution into a second solution and a pharmaceutically acceptable excipient, wherein the second solution comprises water or SLS, and a volume ratio of the first solution and the second solution is between 8:1 and 1:1; and (c) drying and compressing the mixture in step (b) to form a very slightly soluble drug with solid composition.

13 Claims, 4 Drawing Sheets

METHOD OF PREPARING VERY SLIGHTLY SOLUBLE DRUG WITH SOLID DOSAGE FORM

BACKGROUND OF THE INVENTION

1. Field of the Invention

The present invention relates to a method of preparing a very slightly soluble drug with solid dosage form. More particularly, the present invention relates to a method of preparing a very slightly soluble drug such as improved β-Carboline compound or Triazole.

2. Description of the Prior Art

Since β-Carboline or Triazole compounds are water-insoluble, certain methods have been developed to increase the dissolution rate. PCT Application WO 96/38131 and U.S. Pat. No. 5,985,326) disclose co-precipitation technology. Said technology prepares a drug by forming co-precipitates of a β-Carboline compound and a polymeric material such as hydroxypropyl methyl cellulose phthalate, wherein the co-precipitates are subsequently milled and mixed with the excipient, and then compressed into tablets for oral administration. However, the difficulties arose in generating precisely reproducible lots of coprecipitate product, which makes use of coprecipitates less than ideal in pharmaceutical formulations. Additionally, clinical studies involving administration of coprecipitate tablets preliminarily revealed that maximum blood concentration of the β-carboline compound is achieved in 3 to 4 hours, with the average time for onset of therapeutic effect not yet precisely determined. In the treatment of sexual dysfunction, such as male erectile dysfunction or female sexual arousal disorder, however, a more rapid achievement of maximum blood concentration, along with a greater prospect for rapid onset of therapeutic effect, frequently is sought by individuals desiring more immediate and/or less prolonged effects. Accordingly, a need in the art continues to exist for orally administrable β-carboline compounds and 5-carboline-containing pharmaceutical compositions having an ability to provide a therapeutic effect within a desirable, or at least acceptable, time frame.

Taiwan Patent No. 1235658 discloses a particulate preparations technology of a free drug form and provides particulate preparations of a free drug form of a β-Carboline compound having specific and defined particle size characteristics. U.S. Pat. No. 8,288,394 also discloses a micronized Voriconazole compound having specific and defined particle size characteristics. When 90% of the Voriconazole compound medicament have a particle size less than 150 μm, especially a specific surface area from 0.5 $m^2/g$ to 2 $m^2/g$ and a Sauter dia meter from 4 μm to 20 μm, this may effectively overcome the insoluble problem of many medicaments. Although the defined particle size may result in an evenly blended stable pharmaceutical composition with increased dissolution rate, it is extremely difficult to find a source of raw materials having specific and defined particle size characteristics, and the quality control thereof also becomes difficult. Consequently, stock preparation and manufacturing may require a lot of time and cost, thus restricting the scope of this technology in practical applications. Therefore, there remains a need for an improved method of preparing the pharmaceutical composition of β-Carboline or Voriconazole compounds while simultaneously increasing the dissolution rate and the bioavailability in the human body.

SUMMARY OF THE INVENTION

The present invention provides a method of preparing a very slightly soluble drug with solid dosage form, especially for the pharmaceutical composition of β-Carboline or Voriconazole compounds.

According to one embodiment of the present invention, preparing a very slightly soluble drug includes the following steps: (a) adding a very slightly soluble drug into an organic solvent and polysorbate to form a first solution; (b) adding the first solution into a second solution and a pharmaceutically acceptable excipient, wherein the second solution comprises water or sodium lauryl sulfate (SLS), and a volume ratio of the first solution and the second solution is between 8:1 and 1:1; and (c) drying and compressing the mixture in step (b) to form a very slightly soluble drug with solid dosage form.

The present invention provides a method of preparing a very slightly soluble drug with solid dosage form by using a special formulation of the first solution and the second solution. The dissolved rate of the drug may be increased and the production method is not limited by the particle size of the drug through using the special formulation. The present invention provides a special proportion of dosage form having more outstanding dissolved effect than other commercially available drugs and significantly upgraded absorption of the drug in vivo.

DETAILED DESCRIPTION

To provide a better understanding of the presented invention, preferred embodiments will be described in detail. The preferred embodiments of the present invention are illustrated in the accompanying drawings with numbered elements.

The main objective of the present invention is to provide a method of preparing a very slightly soluble drug with solid dosage form. The oral tablets prepared by the present invention preferably use a wet granulated method. The granulation method can be divided into wet granulation and dry granulation, wherein said "wet" granulation requires added water or solvents to effectively bind the active ingredient and non-active ingredients (excipients) into specific shapes, and said "dry" granulation omits the step of adding water or solvents, and thus can directly conduct the powdered molding compression without drying. The "dry" granulation process may add a binding agent and lubricant. Some raw materials having loose density, relatively lighter proportion and poor flowability may be improved by dry granulation, thereby becoming raw materials or end products having high density, heavy proportion and good flowability.

Figure 1:
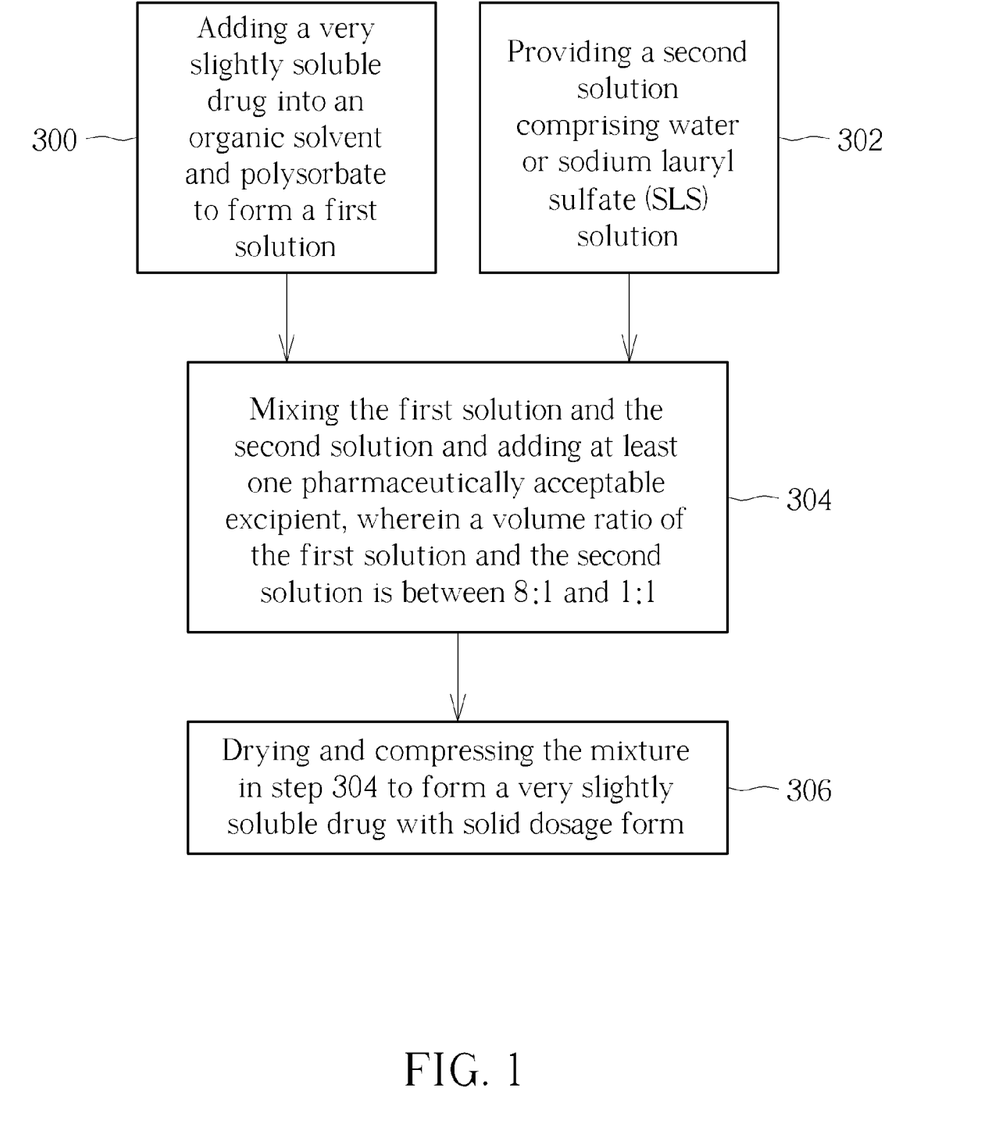
FIG. 1 is a flowchart showing a method of preparing a very slightly soluble drug with solid dosage form according to an embodiment of the invention.

FIG. 1 shows a flowchart of a method of preparing a very slightly soluble drug with solid dosage form according to an embodiment of the invention. The steps of the present invention include:

Step 300: Adding a very slightly soluble drug into an organic solvent and polysorbate to form a first solution;

Step 302: Providing a second solution comprising water or sodium lauryl sulfate (SLS) solution;

Step 304: Mixing the first solution and the second solution and adding at least one pharmaceutically acceptable excipient, wherein a volume ratio of the first solution and the second solution is between 8:1 and 1:1;

Step 306: Drying and compressing the mixture in step 304 to form a very slightly soluble drug with solid dosage form.

The further details of each step are described in the following.

In Step 300, a very slightly soluble drug is added into an organic solvent and polysorbate, after being completely dissolved, to form a first solution. The term "drug" used herein refers to the various bulk drugs and formulations, including various drugs for use in the diagnosis, treatment, mitigation or prevention of disease, or other drugs that affect the body structure and physiological functions of human beings, or the chemical components used in preparation of the aforementioned drugs. The term "very slightly soluble drug" used herein refers to the drugs having a dissolving ratio of drug to solvent greater than 1,000, so it can be completely dissolved in accordance with United States Pharmacopoeia (USP) standards. In one embodiment, the very slightly soluble drug includes β-Carboline compound or Triazole compound. The β-Carboline compound may be, for example, Tadalafil having an aqueous solubility of 2 g/1,000,000 ml. The Triazole compound may be, for example, Voriconazole or Itraconazole having aqueous solubility of 1 g/10,000 ml and 1 g/1,000 ml respectively. It is noteworthy that the drug production method of the present invention can easily prepare a solid medicine form of the very slightly soluble drug. Therefore, the particle size of the very slightly soluble drugs is not particularly limited. A very slightly soluble drug of less than 150 microns cannot be easily produced, but its production can be easily accomplished by the present invention. Thus, in one embodiment, at least 90% of particles in the very slightly soluble drugs have a particle size greater than 150 microns. In another embodiment, at least 90% of particles in the very slightly soluble drugs have a particle size between 150 microns and 40 microns. In another embodiment, at least 90% of particles in the very slightly soluble drugs have a particle size greater than 40 microns.

The organic solvents of the present invention are any solvents having polarity. In one embodiment, the organic solvents refer to solvents having a polarity index between 5.0 and 7.0; preferably, between 5.8 and 6.7. More preferably, the polarity index range of the organic solvent is about 6.5 to the subsequent granulation to increase the powder flowability and binding in order to enhance the efficiency of the powdered molding. Table 1 below shows the polarity index of the commonly used solvents.

TABLE 1

| Solvents | Polarity Index |
| --- | --- |
| Pentane | 0.0 |
| 1,1,2-Trichlorotrifluoroethane | 0.0 |
| Cyclopentane | 0.1 |
| Heptane | 0.1 |
| Hexane | 0.1 |
| Iso-Octane | 0.1 |
| Petroleum Ether | 0.1 |
| Cyclohexane | 0.2 |
| n-Butyl Chloride | 1.0 |
| Trichloroethylene | 1.0 |
| Carbon tetrachloride | 1.6 |
| Di-Iso-Propyl Ether | 2.2 |
| Toluene | 2.4 |
| Methyl t-Butyl Ether | 2.5 |
| o-Xylene | 2.5 |
| Benzene | 2.7 |
| Chlorobenzene | 2.7 |
| o-Dichlorobenzene | 2.7 |
| Ethyl Ether | 2.8 |
| Dichloromethane | 3.1 |
| 1,2-Dichloroethane | 3.5 |
| Ethylene Dichloride | 3.5 |
| n-Butyl Alcohol | 3.9 |
| Isopropyl Alcohol | 3.9 |
| n-Butyl Acetate | 4.0 |
| Isobutyl Alcohol | 4.0 |
| Methyl Isoamyl Ketone | 4.0 |
| n-Propyl Alcohol | 4.0 |
| Tetrahydrofuran | 4.0 |
| Chloroform | 4.1 |
| Methyl Isobutyl Ketone | 4.2 |
| Ethyl Acetate | 4.4 |
| Methyl n-Propyl Ketone | 4.5 |
| Methyl Ethyl Ketone | 4.7 |
| 2-Butanone | 4.7 |
| 1,4-Dioxane | 4.8 |
| Acetone | 5.1 |
| Methanol | 5.1 |
| Ethanol | 5.2 |
| Pyridine | 5.3 |
| 2-Methoxyethanol | 5.5 |
| Acetonitrile | 5.8 |
| Propylene Carbonate | 6.1 |
| Acetic Acid | 6.2 |
| N,N-Dimethylformamide | 6.4 |
| Dimethyl Acetamide | 6.5 |
| N-Methylpyrrolidone | 6.7 |
| Dimethyl Sulfoxide | 7.2 |
| Water | 10.2 |

According to Table 1, the solvents having a polarity index in the range of 5.0-7.0 include acetone, methanol, ethanol, pyridine, 2-methoxyethanol, acetonitrile, propylene carbonate, acetic acid, N,N-dimethylformamide, N,N-dimethyl acetamide, and N-methylpyrrolidone. The preferred polarity index range of the organic solvents is about 5.8-6.7, including acetonitrile, propylene carbonate, acetic acid, N,N-dimethylformamide, N,N-dimethyl acetamide, and N-methylpyrrolidone. The most preferred polarity index range of the organic solvents is about 6.5, including N,N-dimethyl acetamide (DMA). The organic solvents having the enumerated above polarity index range are only examples and persons having ordinary skill in the art should understand that organic solvents having the polarity index are not limited thereto. Moreover, the polysorbate in step 300 may be various polysorbates having different polymerization degree, including polysorbate 20, polysorbate 21, polysorbate 40, polysorbate 60, polysorbate 61, polysorbate 65, polysorbate 80, polysorbate 81, polysorbate 85, and polysorbate 120. Polysorbate 80 (TWEEN 80) is used in the preferred embodiment of the present invention. It should be noted that the added sequence of solvent, polysorbate and the very slightly soluble drug in step 300 can arranged arbitrarily. The preferred sequence adds a very slightly soluble drug into an organic solvent and stirs until completely dissolved, and then adds polysorbate, but is not limited thereto. In one embodiment, the components are completely dissolved by using magnets for stirring and heating to a suitable temperature (e.g. 60° C.) to form a first solution.

In step 302, said second solution comprises water and/or sodium lauryl sulfate (SLS) solution. In one embodiment, the second solution is DI water. In another embodiment, the second solution is SLS aqueous.

In step 304, the first solution is mixed with the second solution, and optionally, any pharmaceutically acceptable excipient or carrier is added. In one embodiment, the excipients used in granulated are sieved through a mesh with 30 sieves to remove agglomerates and subsequently placed in the high-speed granulator. Then, the first solution and the second solution, in the ratio of about 8:1-1:1, are added into the high-speed granulator to mix and granulate. The preferably mixed ratio is about 4:1-5:1; most preferably, about 2:1. The term "excipient or carrier" used herein refers to various other substances used in drug production which are not the active ingredient, for example, various diluents, disintegration agents, binding agents, wetting agents or lubricants, etc. In one embodiment, the diluents are, for example, lactose hydrate and microcrystalline cellulose; the disintegration agents are, for example, cross-linked sodium carboxymethyl cellulose and sodium carboxymethyl starch; the binding agents are, for example, hydroxypropyl cellulose and polyvinylpyrrolidone; and the lubricants are, for example, magnesium stearate and stearic acid. The method and amount of aforementioned excipient may be known by referring to Handbook of Pharmaceutical Excipients, 6th Edition, Amer. Pharm. Assoc. (2009). In one embodiment, the amounts of the various excipients are shown in Table 2.

TABLE 2

| Excipient name (function) | Weight percentage (%) |
|---|---|
| lactose hydrate (diluent) | 15~75% |
| microcrystalline cellulose (diluent) | 20~90% |
| hydroxypropyl cellulose (binding agent) | 1~5% |
| cross-linked sodium carboxymethyl cellulose (disintegration agent) | 0.5~5% |
| magnesium stearate (lubricant) | 0.25~5% |

Finally, as shown in step 306, the mixture of the first solution and the second solution is dried and compressed to form a solid dosage form. The solid dosage forms are, for example, tablets, lozenges, sublingual tablets, dragees, enteric tablets, film-coated tablets, chewable tablets, foaming tablets, and capsules and long-acting release tablets, but are not limited thereto. In one embodiment, after the aforementioned granulation step is accomplished, the wet clot is sieved through a mesh with sieves to remove the agglomerates and increase the drying efficiency. The fluidized bed dryer or the drying oven may be used for drying until the water content is 0.1-2% wt, wherein the temperature may be set at 50-90° C. In one embodiment, if the organic solvent is DMA, the residual amounts thereof are controlled to less than 1,090 ppm to comply with pharmaceutical regulatory requirements. After drying achieves standard, the dried granules are sieved through a mesh with 30 sieves to remove the agglomerates to form a first mixture. Next, the additional excipients such as microcrystalline cellulose, cross-linked sodium carboxymethyl cellulose and magnesium stearate are sieved through a mesh with 30 sieves to remove the agglomerates, and subsequently added into the aforementioned completely dried granules (first mixture) and mix evenly to form a second mixture. The mixed granules undergo powdered molding in an appropriate tablet mold and tablet machine to form a solid dosage form. In one embodiment, the weight percentage of polysorbate in the final solid dosage form (comprising added component after granulation) is 0.1-0.6% wt, for example, is 0.3% wt; and the weight percentage of sodium lauryl sulfate is less than or equal to 1.0% wt. Furthermore, the pure water and N,N-dimethyl acetamide used in the present method are removed during preparation of the tablet and the standard residual amount is established to ensure the product quality. Therefore, the preferred final solid dosage form does not present the N,N-dimethyl acetamide or present in an amount of less than 1,090 ppm.

The following provides some examples and comparative examples, and related experiments to prove the efficacy of the present invention.

Example 1

A formulation for preparing a thousand of tablets contains 20 mg of Tadalafil as the principal component.

| Component name (granulated components) | Weight (g) |
|---|---|
| Tadalafil (at least 90% of the particles (D90) >40 microns) | 20 |
| sodium lauryl sulfate (SLS) | 3.5 |
| pure water | 50 |
| lactose hydrate | 201 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 50 g of pure water.

The preparing process of Example 1: (Example 1 prepares the tablet by wet granulation)
1. First, dissolve Tadalafil in 40 g of pure water and stir with magnets until completely mixed as for the first solution used in granulation.
2. Next, dissolve SLS in 10 g of pure water and stir with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. Stepwise adding of the first solution and the second solution in the ratio of 2:1 into the high-speed granulator to granulate.
5. After the granulation step is completed, the wet clot is sieved through a mesh to remove the agglomerates and increase the drying efficiency. The wet clot is dried with the fluidized bed dryer.

6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are carried out. The pure water used in the present preparing method is removed below the standard residual amount during the preparing processes.

Example 2

A formulation for preparing a thousand of tablets contains 20 mg of Tadalafil as the principal component.

| Component name (granulated components) | Weight (g) |
|---|---|
| Tadalafil (at least 90% of the particles (D90) >40 microns) | 20 |
| N,N-dimethyl acetamide (DMA) | 40 |
| sodium lauryl sulfate (SLS) | 3.5 |
| pure water | 10 |
| lactose hydrate | 201 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 2: (Example 2 prepares the tablet by wet granulation)
1. First, Tadalafil is dissolved in pharmaceutical grade N,N-dimethyl acetamide (DMA), stirred with magnets and heated to 60° C. until completely mixed as for the first solution used in granulation.
2. Next, SLS is dissolved in 10 g of pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are carried out. The pure water and pharmaceutical grade N,N-dimethyl acetamide used in the present preparing method are removed below the standard residual amount during the preparing processes.

Example 3

A formulation for preparing a thousand of tablets contains 20 mg of Tadalafil as the principal component.

| Component name (granulated components) | Weight (g) |
|---|---|
| Tadalafil (at least 90% of the particles (D90) >40 microns) | 20 |
| Tween 80 | 0.4 |
| N,N-dimethyl acetamide (DMA) | 40 |
| sodium lauryl sulfate (SLS) | 3.5 |
| pure water | 10 |
| lactose hydrate | 200.6 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 3: (Example 3 prepares the tablet by wet granulation)
1. First, Tadalafil and Tween 80 are dissolved in pharmaceutical grade N,N-dimethyl acetamide (DMA), stirred with magnets and heated to 60° C. simultaneously until completely mixed as for the first solution used in granulation.
2. Next, SLS is dissolved in pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.

8. The evenly mixed granules undergo powdered molding in an appropriate tablet mold and tablet machine.
9. After the powdered molding is accomplished, the film-coated cladding processes are performed. The pure water and pharmaceutical grade N,N-dimethyl acetamide used in the present preparing method are removed below the standard residual amount during the preparing processes.

Example 4

A formulation for preparing a thousand of tablets contains 20 mg of Tadalafil as the principal component.

| Component name (granulated components) | Weight (g) |
| --- | --- |
| Tadalafil (at least 90% of the particles (D90) >40 microns) | 20 |
| Tween 80 | 1 |
| N,N-dimethyl acetamide (DMA) | 40 |
| sodium lauryl sulfate (SLS) | 3.5 |
| pure water | 10 |
| lactose hydrate | 200 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 4: (Example 4 prepares the tablet by wet granulation)
1. First, Tadalafil and Tween 80 are dissolved in pharmaceutical grade N,N-dimethyl acetamide (DMA), stirred with magnets and heated to 60° C. simultaneously until completely mixed as for the first solution used in granulation.
2. Next, SLS is dissolved in pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are performed. The pure water and pharmaceutical grade N,N-dimethyl acetamide used in the present preparing method are removed below the standard residual amount during the preparing processes.

Example 5

A formulation for preparing a thousand of tablets contains 20 mg of Tadalafil as the principal component.

| Component name (granulated components) | Weight (g) |
| --- | --- |
| Tadalafil (at least 90% of the particles (D90) >40 microns) | 20 |
| Tween 80 | 2 |
| N,N-dimethyl acetamide (DMA) | 40 |
| sodium lauryl sulfate (SLS) | 3.5 |
| pure water | 10 |
| lactose hydrate | 199 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 5: (Example 5 prepares the tablet by wet granulation)
1. First, Tadalafil and Tween 80 are dissolved in pharmaceutical grade N,N-dimethyl acetamide (DMA), stirred with magnets and heated to 60° C. simultaneously until completely mixed as for the first solution used in granulation.
2. Next, SLS is dissolved in pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are performed. The pure water and pharmaceutical grade N,N-dimethyl acetamide used in the present preparing method are removed below the standard residual amount during the preparing processes.

Example 6

A formulation for preparing a thousand of tablets contains 20 mg of Tadalafil as the principal component.

| Component name (granulated components) | Weight (g) |
| --- | --- |
| Tadalafil (at least 90% of the particles (D90) >40 microns) | 20 |
| N,N-dimethyl acetamide (DMA) | 40 |
| pure water | 10 |
| lactose hydrate | 204.5 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 6: (Example 6 prepares the tablet by wet granulation)
1. First, Tadalafil is dissolved in pharmaceutical grade N,N-dimethyl acetamide (DMA), stirred with magnets and heated to 60° C. simultaneously until completely mixed as for the first solution used in granulation.
2. Next, 10 g of pure water is weighed as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, conducting the film-coated cladding processes are performed. The pure water and pharmaceutical grade N,N-dimethyl acetamide used in the present preparing method are removed below the standard residual amount during the preparing processes.

Example 7

A formulation for preparing a thousand of tablets contains 20 mg of Tadalafil as the principal component.

| Component name (granulated components) | Weight (g) |
| --- | --- |
| Tadalafil (at least 90% of the particles (D90) >40 microns) | 20 |
| N,N-dimethyl acetamide (DMA) | 40 |
| sodium lauryl sulfate (SLS) | 1.75 |
| pure water | 10 |
| lactose hydrate | 202.75 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 1: (Example 1 prepares the tablet by wet granulation)
1. First, Tadalafil is dissolved in pharmaceutical grade N,N-dimethyl acetamide (DMA), stirred with magnets and heated to 60° C. until completely mixed as for the first solution used in granulation.
2. Next, SLS is dissolved in pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are performed. The pure water and pharmaceutical grade N,N-dimethyl acetamide used in the present preparing method are removed below the standard residual amount during the preparing processes.

Example 8

A formulation for preparing a thousand of tablets contains 20 mg of Tadalafil as the principal component.

| Component name (granulated components) | Weight (g) |
| --- | --- |
| Tadalafil (at least 90% of the particles (D90) >40 microns) | 20 |

13 -continued

| Component name (granulated components) | Weight (g) |
|---|---|
| N,N-dimethyl acetamide (DMA) | 40 |
| sodium lauryl sulfate (SLS) | 3.5 |
| pure water | 10 |
| lactose hydrate | 201 |
| hydroxypropyl cellulose | 3.5 |
| cross-linked sodium carboxymethyl cellulose | 7 |
| (added component after granulation) | |
| microcrystalline cellulose | 104.5 |
| cross-linked sodium carboxymethyl cellulose | 7 |
| magnesium stearate | 3.5 |
| total* | 350 |

*note:
the total weight does not contain 10 g of pure water and 40 g of DMA.

The preparing process of Example 8: (Example 8 prepares the tablet by wet granulation)
1. First, Tadalafil is dissolved in pharmaceutical grade N,N-dimethyl acetamide (DMA), stirred with magnets and heated to 60° C. until completely mixed as for the first solution used in granulation.
2. Next, SLS is dissolved in 10 g of pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are performed. The pure water and pharmaceutical grade N,N-dimethyl acetamide used in the present preparing method are removed below the standard residual amount during the preparing processes.

Example 9

A formulation for preparing a thousand of tablets contains 200 mg of Voriconazole as the principal component.

| Component name (granulated components) | Weight (g) |
|---|---|
| Voriconazole (at least 90% of the particles (D90) >150 microns) | 200 |

14 -continued

| Component name (granulated components) | Weight (g) |
|---|---|
| Tween 80 | 2 |
| sodium lauryl sulfate (SLS) | 6 |
| pure water | 100 |
| lactose hydrate | 236 |
| hydroxypropyl cellulose | 6 |
| cross-linked sodium carboxymethyl cellulose | 12 |
| (added component after granulation) | |
| microcrystalline cellulose | 120 |
| cross-linked sodium carboxymethyl cellulose | 12 |
| magnesium stearate | 6 |
| total* | 600 |

*note:
the total weight does not contain 100 g of pure water.

The preparing process of Example 9: (Example 9 prepares the tablet by wet granulation)
1. First, Voriconazole and Tween 80 are dissolved in 80 g of pure water and stirred with magnets until completely mixed as for the first solution used in granulation.
2. Next, SLS is dissolved in 20 g of pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator to granulate.
5. After the granulation step is completed, the wet clot is sieved through a mesh to remove the agglomerates and increase the drying efficiency. The wet clot is dried with the fluidized bed dryer.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are performed. The pure water used in the present preparing method is removed below the standard residual amount during the preparing processes.

Example 10

A formulation for preparing a thousand of tablets contains 200 mg of Voriconazole as the principal component.

| Component name (granulated components) | Weight (g) |
|---|---|
| Voriconazole (at least 90% of the particles (D90) >150 microns) | 200 |
| Tween 80 | 2 |
| sodium lauryl sulfate (SLS) | 6 |
| N,N-dimethyl acetamide (DMA) | 80 |

-continued

| Component name (granulated components) | Weight (g) |
|---|---|
| pure water | 20 |
| lactose hydrate | 236 |
| hydroxypropyl cellulose | 6 |
| cross-linked sodium carboxymethyl cellulose | 12 |
| (added component after granulation) | |
| microcrystalline cellulose | 120 |
| cross-linked sodium carboxymethyl cellulose | 12 |
| magnesium stearate | 6 |
| total* | 600 |

*note:
the total weight does not contain 20 g of pure water and 80 g of DMA.

The preparing process of Example 10: (Example 10 prepares the tablet by wet granulation)
1. First, Voriconazole and Tween 80 are dissolved in N,N-dimethyl acetamide (DMA), stirred with magnets and heated to 60° C. until completely mixed as for the first solution used in granulation.
2. Next, SLS is dissolved in 20 g of pure water and stirred with magnets until completely dissolved as for the second solution used in granulation.
3. The excipients used in granulated (e.g. lactose hydrate, hydroxypropyl cellulose and cross-linked sodium carboxymethyl cellulose) are sieved through a mesh to remove the agglomerates and subsequently placed in the high-speed granulator.
4. The first solution and the second solution in the ratio of 2:1 are added into the high-speed granulator for granulation.
5. After the granulation step is completed, the wet clot is sieved through a mesh to remove the agglomerates and increase the drying efficiency. The wet clot is dried with the fluidized bed dryer. The residual amount of DMA is controlled to be less than the standard residual amount.
6. After drying achieves standard, the dried granules are sieved through a mesh to remove the agglomerates to form a first mixture.
7. Then, the additional excipients (e.g. microcrystalline cellulose, cross-linked sodium carboxymethyl cellulose and magnesium stearate) are sieved through a mesh to remove the agglomerates, and subsequently added into the aforementioned dried granules (first mixture) and mixed evenly to form a second mixture.
8. The evenly mixed granules undergo powdered molding in an appropriate tablet mold and tablet machine.
9. After the powdered molding is accomplished, the film-coated cladding processes are performed. The pure water and pharmaceutical grade N,N-dimethyl acetamide used in the present preparing method are removed below the standard residual amount during the preparing processes.

Comparative Experiment 1

Experimental research had been performed in vivo to demonstrate the improvements in the bioavailability of the pharmaceutical compositions prepared by the present invention. The research is a random crossover study conducted for healthy men aged between 22 and 32 years old. The following table lists the pharmacokinetics parameters in vivo of oral tablet containing 20 mg of Tadalafil as the principal component, and illustrates the efficacy performances of the drugs prepared by different preparing process conditions as compared with the original brand drug.

The results show that the preparing method of pharmaceutical compositions of the present invention (i.e. Example 4) is indeed better than the general preparing method (i.e. Example 1). The present invention obviously enhances the bioavailability of human ($C_{max}$ & $AUC_{0-24}$), decreases the achieved time of the maximum blood concentration ($T_{max}$) of β-Carboline compounds (Tadalafil), and can achieve the bioequivalence with the original brand drug.

| | Test drug | | |
|---|---|---|---|
| pharmacokinetics parameter | Commercial drug (Cialis®) | Example 1 | Example 4 |
| $C_{max}$ (microgram/l) | 353 | 258 | 331 |
| $T_{max}$ (hr) | 2.9 | 3.9 | 2.8 |
| $AUC_{0-24}$ (microgram · hr/l) | 9181 | 7936 | 8853 |

Comparative Experiment 2

Figure 2:
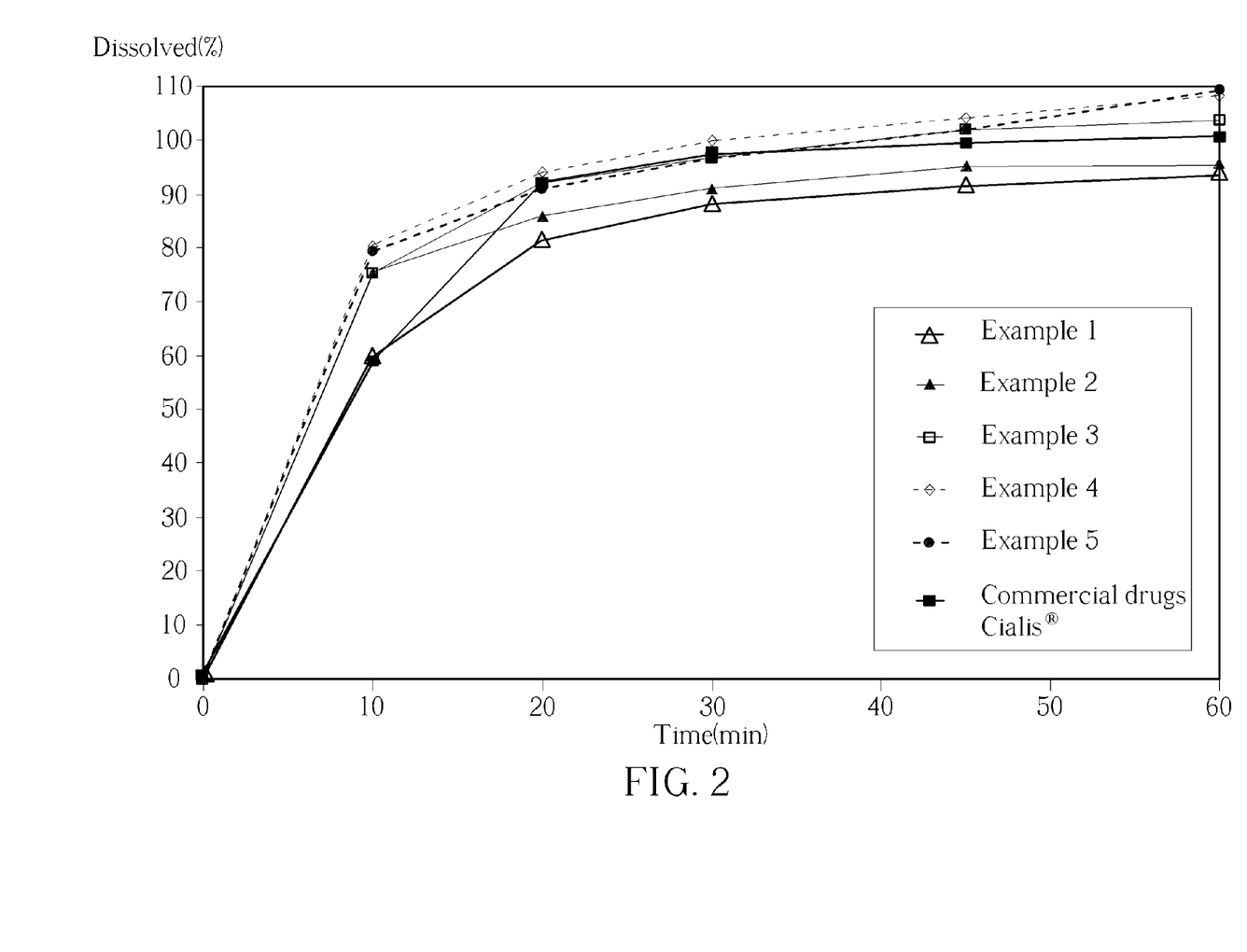
FIG. 2 is a diagram which plots the percentage of tablets containing the principal component (Tadalafil) which are dissolved versus time to illustrate the dissolution characteristics obtained from the different process and formulations conditions of the present invention and those obtained from the commercial drug Cialis®.

A comparison was conducted between the commercial drugs and the aforementioned examples of the present invention to prove the drugs formed by the present preparing method have dissolution efficacy. According to the preceding description, Examples 1-5 are the preparing method of drugs containing Tadalafil as the principal component, wherein DMA and Tween 80 are not added in Example 1. DMA is added in Examples 2-5, and the concentration of Tween 80 in Examples 2-5 is 0%, 0.1%, 0.28% and 0.57% respectively. The present invention has also been compared with the commercial drug Cialis®. FIG. 2 shows the percentage of tablets containing the principal component (Tadalafil) which are dissolved versus time to illustrate the dissolution characteristics obtained from the different process and formulations conditions of the present invention and those obtained from the commercial drug Cialis®. The conditions of the dissolution test are according to the method provided by the United States Pharmacopoeia (USP method), wherein the device is a paddle drug dissolution test system, the rotational speed is 50 rpm, the solvent is 1000 ml of water+0.5% (w/w) SLS and the sampling points are 10 minutes, 20 minutes, 30 minutes, 45 minutes, and 60 minutes. As shown in FIG. 2, comparing β-Carboline compounds (Tadalafil) prepared by Examples 2-5 of the present invention with Example 1, the present invention obviously enhances the dissolution rate of drugs. This means that adding Tween 80 and DMA can increase the dissolution rate of drugs. Moreover, as the concentration of Tween 80 increases, the dissolution rate increases accordingly. Comparing Examples 1-5 with commercial drug Cialis® shows an equivalent dissolution rate, and Examples 3-5 show an improved dissolution rate, wherein the preferred formulation contains more than 0.1% of Tween 80; preferably, 0.28% of Tween 80 (Example 4).

Comparative Experiment 3

Figure 3:
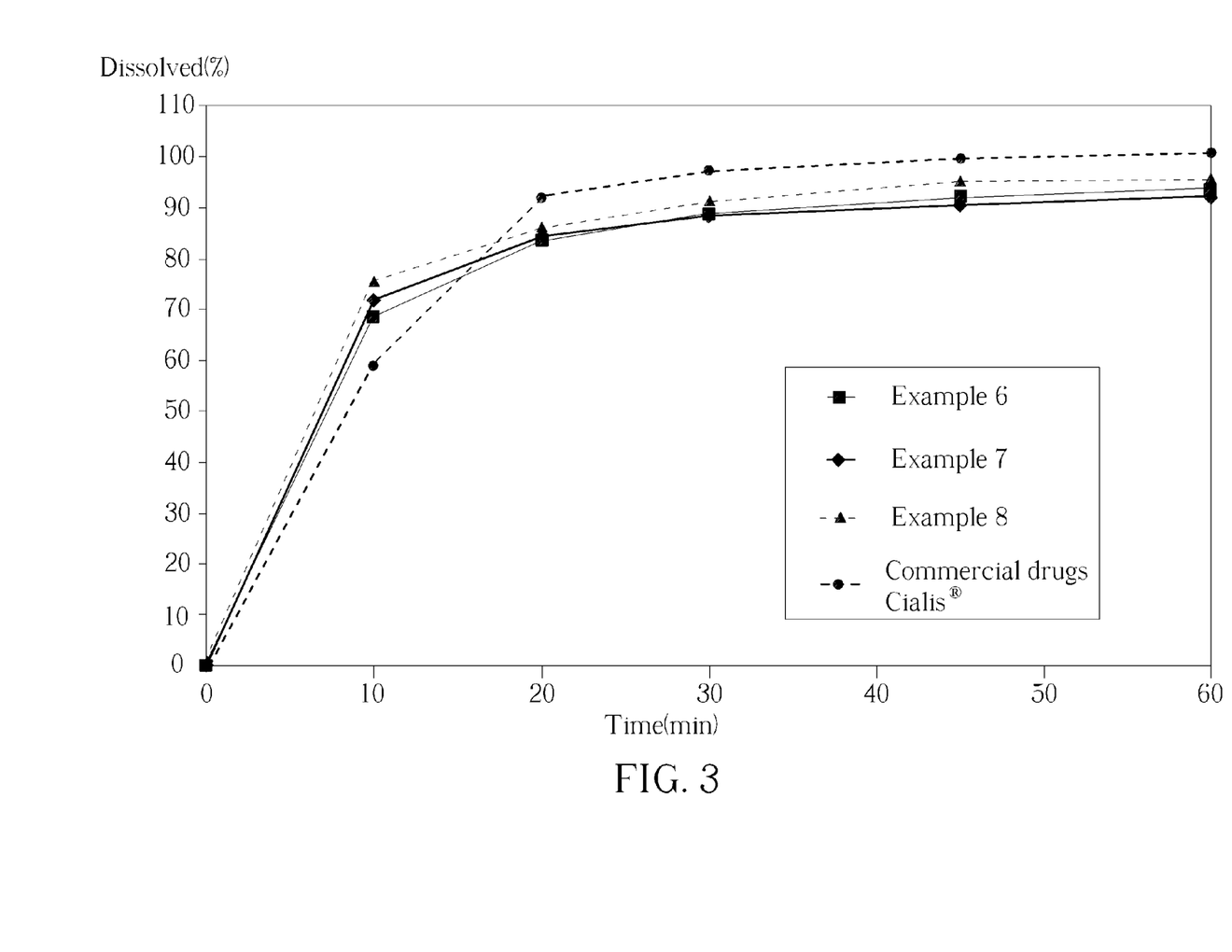
FIG. 3 is a diagram which plots the percentage of tablets containing the principal component (Tadalafil) which are dissolved versus time to illustrate the dissolution characteristics obtained from the different process and formulations conditions of the present invention and those obtained from the commercial drugs Cialis®.

According to the preceding description, Examples 6-8 are the preparing method of drugs containing Tadalafil as the principal component, wherein Examples 6-8 all have DMA and SLS, and the concentration of SLS in Examples 6-8 is 0%, 0.5% and 1.0% respectively. FIG. 3 shows the percentage of tablets containing the principal component (Tadalafil) which are dissolved versus time to illustrate the dissolution characteristics obtained from the different process and formulations conditions of the present invention and those obtained from the commercial drug Cialis®, wherein experimental parameters are the same as Comparative Experiment 2. As shown in FIG. 3, Examples 6-8 of the present invention obviously enhance the dissolution rate of β-Carboline compounds (Tadalafil), particularly the formulation containing more than 0.5% of SLS, and preferably, the formulation containing 1.0% of SLS (Example 8). Comparing Examples 6-8 with commercial drug Cialis®, SLS added in Examples 6-8 may increase the dissolution rate of drugs in a shorter time. For example, the dissolution rate of the present invention is higher than Cialis® at 10 minutes, and therefore has more practicality in the treatment of male erectile dysfunction.

Comparative Experiment 4

Figure 4:
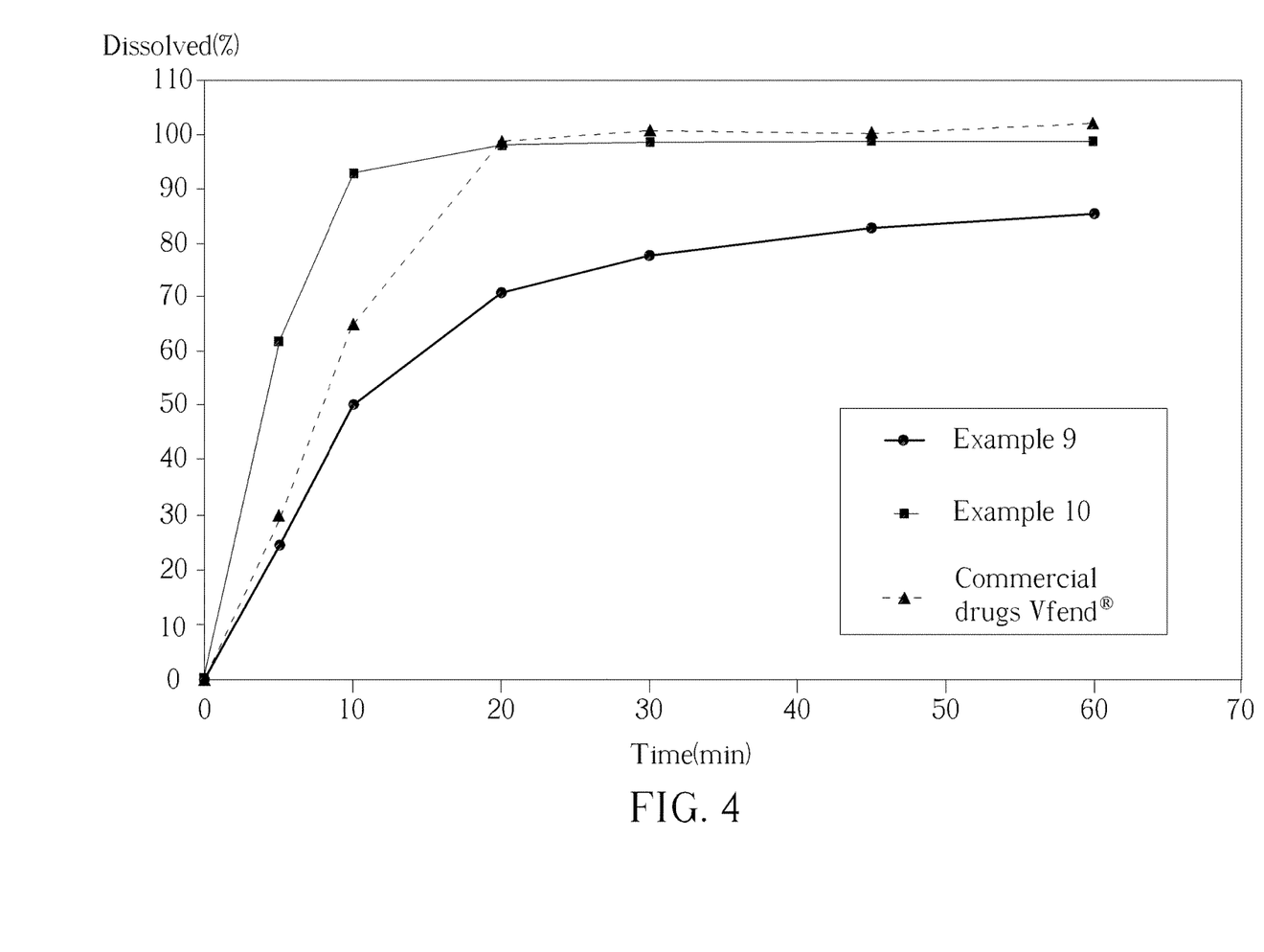
FIG. 4 is a diagram which plots the percentage of tablets containing the principal component (Voriconazole) which are dissolved versus time to illustrate the dissolution characteristics obtained from the different process and formulations conditions of the present invention and those obtained from the commercial drugs Vfend®.

According to the preceding description, Example 9 and Example 10 are preparation methods of drugs containing Voriconazole as the principal component. As seen by comparing Example 9 and Example 10, DMA is not added in Example 9. FIG. 4 shows the percentage of tablets containing the principal component (Voriconazole) which are dissolved versus time to illustrate the dissolution characteristics obtained from the different process and formulations conditions of the present invention and those obtained from the commercial drugs Vfend®. The conditions of dissolution test are tested according to the method provided by the United States Pharmacopoeia (USP method), wherein the device is paddle drug dissolution test system, the rotational speed is 50 rpm, the solvent is 900 ml of 0.1 N HCL solution and the sampling points are 10 minutes, 20 minutes, 30 minutes, 45 minutes, 60 minutes. As shown in FIG. 4, the preparing method of pharmaceutical compositions of the present invention (i.e., Example 10) obviously enhances the dissolution rate of Voriconazole compounds.

To sum up, the present invention provides a method of preparing a very slightly soluble drug with solid dosage form by using a special formulation of the first solution and the second solution. The dissolved rate of the drug may be increased and the production method not limited by the particle size of the drug through using the special formulation. The present invention provides a special proportion of dosage form having greater dissolved effect than other commercially available drugs, as well as significantly upgraded absorption of the drug in vivo.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of preparing a very slightly water soluble drug with a solid dosage form including the following steps:
   (a) Adding a very slightly soluble drug into an organic solvent and a polysorbate to form a first solution;
   (b) Adding the first solution into a second solution and at least one pharmaceutically acceptable excipient to obtain a mixture, wherein the second solution comprises water or sodium lauryl sulfate (SLS), and a volume ratio of the first solution and the second solution is between 8:1 and 1:1; and
   (c) Drying and compressing the mixture in step (b) to form a very slightly soluble drug with a solid dosage form.

2. The method according to claim 1, wherein the very slightly soluble drug is Tadalafil, Itraconazole or Voriconazole.

3. The method according to claim 1, wherein the very slightly soluble drug is Tadalafil or Voriconazole.

4. The method according to claim 1, wherein a polarity index of the organic solvent is 5.8-6.7.

5. The method according to claim 1, wherein a polarity index of the organic solvent is 6.5.

6. The method according to claim 1, wherein the organic solvent comprises pyridine, 2-methoxyethanol, acetonitrile, propylene carbonate, N,N-dimethylformamide, N,N-dimethyl acetamide, or N-methylpyrrolidone.

7. The method according to claim 1, wherein the organic solvent is N,N-dimethyl acetamide.

8. The method according to claim 1, wherein the polysorbate is 0.1-0.6% wt, based on the total amount of the solid dosage form.

9. The method according to claim 1, wherein the polysorbate is 0.3% wt, based on the total amount of the solid dosage form.

10. The method according to claim 1, wherein the polysorbate is polysorbate 80 (Tween 80).

11. The method according to claim 1, wherein the second solution comprises sodium lauryl sulfate and wherein the sodium lauryl sulfate is present in an amount of 1.0% wt, based on the total amount of the solid dosage form.

12. The method according to claim 1, wherein the volume ratio of the first solution and the second solution is between 4:1 and 1.5:1.

13. The method according to claim 1, wherein the volume ratio of the first solution and the second solution is 2:1.

* * * * *